United States Patent [19]

Ruckes et al.

[11] Patent Number: 4,994,611
[45] Date of Patent: Feb. 19, 1991

[54] PROCESS FOR THE PRODUCTION OF N,N'-BIS-(3-AMINOPHENYL)-UREAS

[75] Inventors: Andreas Ruckes; Gerhard Grögler, both of Leverkusen; Richard Kopp, Cologne, all of Fed. Rep. of Germany

[73] Assignee: Bayer Aktiengesellschaft, Leverkusen, Fed. Rep. of Germany

[21] Appl. No.: 436,393

[22] Filed: Nov. 14, 1989

[30] Foreign Application Priority Data

Dec. 23, 1988 [DE] Fed. Rep. of Germany ....... 3843410

[51] Int. Cl.$^5$ ............................................ C07C 273/18
[52] U.S. Cl. ........................................ 564/50; 564/48
[58] Field of Search .......................................... 564/50

[56] References Cited

U.S. PATENT DOCUMENTS

| | | | |
|---|---|---|---|
| 1,617,847 | 2/1927 | Heinze | 564/50 |
| 2,503,797 | 4/1950 | Brunner et al. | 260/553 |
| 3,214,468 | 10/1965 | Frick et al. | 564/50 |

FOREIGN PATENT DOCUMENTS

0624388 7/1961 Canada .................. 564/50

OTHER PUBLICATIONS

I. L. Khmel'nitskaya et al. en Zhurnal Obschei Khimii 30 (2), 1960.

W. R. Turner & L. M. Werbel in J. Med. Chem. 28, 1985.
A. Ostrogovich in Liebigs Ann; 293 1896, on pgs.
DRP 140613, Vom. 4, Dec. 1900 ab.
DRP 268658, Vom. 14, Sep. 1912.

Primary Examiner—Glennon H. Hollrah
Assistant Examiner—Susan P. Treanor
Attorney, Agent, or Firm—Joseph C. Gil; Thomas W. Roy

[57] ABSTRACT

The present invention is directed to a process for the preparation of N,N'-bis-(3-aminophenyl)-ureas corresponding to formula (I)

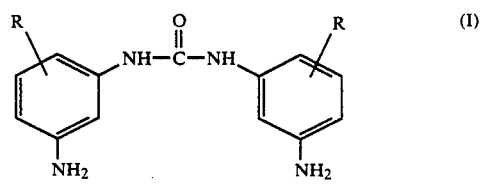

wherein
R represents a linear or branched $C_1$–$C_6$ alkyl group which is in the 2-, 4- and/or 6-position, characterized in that the corresponding phenylene diamines are reacted with urea in a molar ratio of greater than 2:1 in chlorobenzene as solvent.

8 Claims, No Drawings

PROCESS FOR THE PRODUCTION OF N,N'-BIS-(3-AMINOPHENYL)-UREAS

BACKGROUND OF THE INVENTION

1. Field of the Invention

This invention is directed to a process for the production of N,N'-bis-(3-aminophenyl)-ureas by reacting alkyl-substituted m-phenylene diamines with urea in chlorobenzene as solvent.

2. Description of the Prior Art

It is known that diaminodiphenyl ureas can be obtained by phosgenating the corresponding nitroanilines to form the dinitrodiphenyl urea and subsequent catalytic reduction to the diamine, cf. for example the synthesis of III described by I. L. Khmel'nitskaya et al in Zh. Obsh. Khim 30 (2) (1960), page 602, or the synthesis of N,N'-bis-(5-amino-2-methylphenyl)-urea IV described by W. R. Turner and L. M. Werbel in J. Med. Chem. 28 (1985), page 1738.

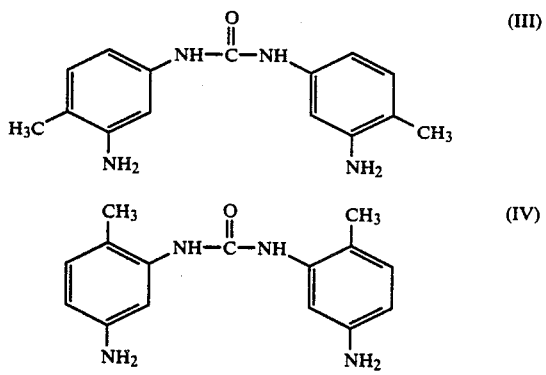

Apart from the generally poor yields of the overall reaction, the primary disadvantage of these syntheses is the expensive reduction step.

Another two-step synthesis for the production of diaminodiphenyl ureas is the reaction of N-acetyl-p-phenylene diamine with urea and subsequent hydrolysis of the protective acetyl group which is described by H. Schiff and A. Ostrogovick in Liebigs Ann., 293, 1896, on pages 371 et seq with reference to the example of N,N'-bis-(4-aminophenyl)-urea. The disadvantage of this process is that monoacetylated diamines, which are generally not easy to prepare, have to be used as starting components.

Special p-phenylene diamines, in which the reactivity of an $NH_2$ group is greatly reduced by suitable o-substituents, can be directly reacted with phosgene to form the corresponding aminocarbanilides. Suitable diamines include 2,5-diaminosulfonic acid (DRP 140613, Frl. 11, 1292) or 2,6-dichloro-p-phenylene diamine (DRP 268658, Frl. 11, 164). Under these conditions, other phenylene diamines result in polyureas which are totally unsuitable as reactive chain-extending agents.

A simple one-step process is the reaction of p-phenylene diamine with urea in aqueous solution as described in U.S. Pat. No. 2,503,797. Substantially pure N,N-bis-(4-aminophenyl)-urea is obtained in a high yield. However, when m-phenylene diamines are used as starting materials, the corresponding ureas—according to the teaching of the above-mentioned patent—can only be obtained in high yields substantially free from oligomers if four equivalents of sulfuric acid are added. For working up, the sulfuric acid salt of the urea which is precipitated has to be converted by reaction with $BaCl_2$ into the corresponding chloride from which the free base can then be obtained.

Finally, U.S. Pat. No. 1,617,847 describes the production of N,N'-bis-(4-aminophenyl)-ureas by the reaction of p-phenylene diamine and alkyl-substituted p-phenylene diamines with urea in bulk or in inert solvents such as o-dichlorobenzene. However, if 2,4-diaminobenzene (TDA-2,4) is used under the conditions described in the examples of the above-mentioned patent, only an oligourea of low NH value is obtained, which is totally unsuitable for the applications envisaged.

In conclusion, it may be said that previously known processes are either too expensive, are only suitable for special diamines or only provide the desired low molecular weight ureas where p-substituted phenylene diamines are used as starting materials.

An object of the present invention is to provide a simple synthesis for ureas based on ortho-alkyl-substituted phenylene diamines.

Two aspects are of particular significance in this regard. On the one hand, the process should lead to low molecular weight ureas because, as already discussed, polyureas are unsuitable as chain-extending agents due to their inadequate reactivity. On the other hand, the proportion of monomeric starting amine in the urea products should be reduced as much as possible to eliminate (1) any physiological risk in handling the product and (2) the adverse effect which free, aromatic low molecular weight amines are known to have on the stability of the PUR plastics produced with them to light and discoloration.

Surprisingly, this object may be achieved by the reaction of ortho-alkyl-substituted m-phenylene diamines with urea in chlorobenzene as solvent at a molar ratio of phenylene diamine to urea of greater than 2:1.

SUMMARY OF THE INVENTION

The present invention is directed to a process for the preparation of N,N'-bis-(3-aminophenyl)-ureas corresponding to formula (I)

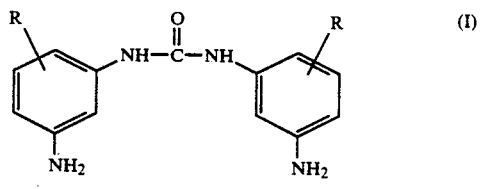

wherein

R represents a linear or branched $C_1$–$C_6$ alkyl group which is in the 2-, 4- and/or 6-position, characterized in that the corresponding phenylene diamines are reacted with urea in a molar ratio of greater than 2:1 in chlorobenzene as solvent.

DETAILED DESCRIPTION OF THE INVENTION

The process according to the invention is based on the reaction of alkyl-substituted m-phenylene diamines with urea in chlorobenzene as solvent. In addition to the desired N,N'-bis-(3-aminophenyl)-ureas corresponding to formula (I), the product may also contain small quantities of oligomeric ureas corresponding to formula (II)

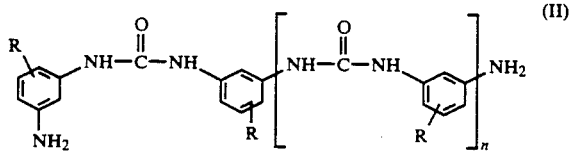

(II)

wherein R is defined as above.

The diaminodiphenyl ureas obtained by the process according to the invention may be used in solid or dissolved form as chain-extending agents for the production of polyurethane polyurea elastomers or pure polyurea elastomers. The diaminodiphenyl ureas according to the invention may also be used, for example, as a coupling component for diazo dyes, as hardeners for epoxy and phenolic resins and for any other known reactions involving amines such as amidation or imidation.

1-alkyl-2,4-diaminobenzenes, such as toluylene-2,4diamine, are particularly suitable for the process according to the present invention. The diaminobenzenes may be used either individually or in admixture with one another.

Only chlorobenzene is suitable as solvent. If solvents other than chlorobenzene, such as o-dichlorobenzene or xylene, are used, the products are unacceptable. Either high molecular weight ureas are obtained or, due to 2,4-diaminotoluene being entrained during precipitation of the urea, the products contain an unacceptably high proportion of monomeric starting diamine which can only be removed by relatively expensive purification (for example recrystallization or the like).

The molar ratio of m-phenylene diamine to urea is greater than 2:1, preferably a molar ratio of 3:1 to 10:1 and, most preferably, in a molar ratio of 3:1 to 5:1. If molar ratios of less than 2:1 are used, products having excessively low NH values, i.e., high molecular weight ureas, are obtained. In the most preferred range, products having NH values close to theoretical are obtained. Although it is possible in principle to increase the molar ratio, this does not improve the product in any way and also is not economical.

The m-phenylene diamines are dissolved in chlorobenzene in quantities of about 20 to 200 parts by weight, preferably about 40 to 150 parts by weight and more preferably about 80 to 120 parts by weight per 100 parts by weight of solvent. Although more dilute solutions are possible in principle, they result in increased chain extension. If, on the other hand, the concentration is excessively increased, the reaction mixture becomes increasingly more difficult to stir because of precipitation of the product and, in addition, contains considerable quantities of entrained starting amine which can only be removed by expensive purification steps. Accordingly, the NH value of the desired urea can be controlled within certain limits through the choice of the concentration of starting amine. In the preferred concentration range, NH values approaching theoretical are obtained.

In accordance with the process of the present invention the urea is added to the solution of the amine in chlorobenzene in the described molar ratio and the reaction mixture is stirred, preferably under reflux, at temperatures of about 60° to 136° C. The precipitated product is filtered off and washed with chlorobenzene to remove residual starting amine. It has been found to be of advantage in this regard to add chlorobenzene before filtration and to carry out filtration in a steam-heated suction filter to prevent the precipitation of residual amine at those temperatures. It is also of advantage for the same reasons to wash the product with hot chlorobenzene, the excess starting amine recovered from the mother liquor may be reused without further purification.

The desired amine is obtained after drying in the form of a finely crystalline solid in excellent yields and with NH values of greater than 270 mg KOH/g (theoretical 416 mg KOH/g), preferably greater than 360 mg KOH/g and more preferably greater than 380 mg KOH/g, depending upon the concentration and reactant ratios selected. The content of free monomeric starting amine is less than 1% by weight, preferably less than 0.5% by weight.

The following examples are intended to illustrate the process according to the invention without limiting it in any way. Percentages are percentages by weight, unless otherwise stated.

EXAMPLES

Example 1

40 kg (327.8 moles) toluylene-2,4-diamine (2,4-TDA; Mp. 98°C.) and 4920 g (82 moles) urea (molar ratio 2,4-TDA/urea 4:1) were added at room temperature to 44 kg chlorobenzene (90 parts by weight 2,4-TDA, based on 100 parts by weight chlorobenzene). The reaction mixture was stirred under reflux for 19 hours in an inert gas atmosphere ($N_2$). After dilution with 140 kg chlorobenzene, the reaction mixture was heated under reflux for another 60 minutes. The precipitated product was filtered through a heatable suction fiber at approximately 100° C., washed 4 times with 50 kg hot chlorobenzene and then dried in a vacuum drying cabinet at 80°C.

Yield: 19.5 kg (89%, based on urea used).

NH value ($HClO_4$/glacial acetic acid): 406 mg KOH/g (theoretical 416 mg KOH/g).

Residual 2,4-TDA content (HPLC): 0.253% by weight.

Example 2

366 g (3 moles) toluylene-2,4-diamine (2,4-TDA) and 51.4 g (0.86 moles) urea (molar ratio 2,4-TDA/urea 3.48:1) were added at room temperature to 366 g chlorobenzene (100 parts by weight 2,4-TDA, based on 100 parts by weight chlorobenzene). The reaction mixture was stirred under reflux for 19 hours. After dilution with 1208 g chlorobenzene, the reaction mixture was heated under reflux for another 30 minutes. The precipitated product was filtered through a steamheated suction filter at approximately 100° C., washed with approximately 500 ml hot chlorobenzene and then dried at 80° C. in a vacuum drying cabinet.

Yield: 199 g (86%, based on urea used).

NH value ($HClO_4$/glacial acetic acid): 405 mg KOH/g (theoretical 416 mg KOH/g).

Residual 2,4-TDA content (HPLC): 0.285% by weight.

Example 3

260 g (2.13 moles) toluylene-2,4-diamine (2,4-TDA) and 49 g (0.814 moles) urea (molar ratio 2,4-TDA/urea 2.62:1) were added at room temperature to 1334 g chlorobenzene (19.5 parts by weight 2,4-TDA, based on 100 parts by weight chlorobenzene). The reaction mixture was stirred under reflux for 12 hours. The precipitated product was filtered off hot, washed with toluene and petroleum ether and then dried in a vacuum drying cabinet.

Yield: 169 g (76.5%, based on urea used).

NH value (HClO4/glacial acetic acid): 336 mg KOH/g.

Residual 2,4-TDA content (HPLC): 0.1% by weight.

Example 4

350 g (2.86 moles) toluylene-2,4-diamine (2,4-TDA) and 43 g (0.716 moles) urea (molar ratio 2,4-TDA/urea 4:1) were added at room temperature to 778 g chlorobenzene (45 parts by weight 2,4-TDA, based on 100 parts by weight chlorobenzene). The reaction mixture was stirred under reflux for 19 hours. After the addition of approximately 1600 g chlorobenzene, the precipitated product was filtered off hot and then dried in a vacuum drying cabinet.

Yield: 170 g (85%, based on urea used)

NH value (HClO4/glacial acetic acid): 407 mg KOH/g.

Residual 2,4-TDA content (HPLC): 0.254% by weight.

Example 5a 1800 g (14.75 moles) toluylene-2,4-diamine (2,4-TDA) and 221 g (3.68 moles) urea (molar ratio 2,4-TDA/urea 4:1) were added at room temperature to 2000 g chlorobenzene (90 parts by weight 2,4-TDA, based on 100 parts by weight chlorobenzene). The reaction mixture was stirred under reflux for 19 hours. After the addition of 6670 g chlorobenzene, the reaction mixture was stirred under reflux for another hour. The precipitated product was filtered off hot through a heatable suction filter, washed with approximately 2 liters hot chlorobenzene and then dried in a vacuum drying cabinet.

Yield: 910 g (91.5%, based on urea used).

NH value (HClO4/glacial acetic acid): 414 mg KOH/g.

Residual 2,4-TDA content (HPLC): 0.417% by weight.

The mother liquor was concentrated to approximately 1900 g. The chlorobenzene recovered was used as solvent in 5b).

Example 5b

Example 5a was repeated.

Yield: 856 g (91.5%, based on urea used).

NH value (HClO4/glacial acetic acid): 395 mg KOH/g.

Residual 2,4-TDA content (HPLC): 0.291% by weight.

The mother liquor was concentrated to approximately 1900 g and combined with the concentrated mother liquor from 5a). The toluylene-2,4-diamine content was approximately 1800 g.

221 g urea were added at room temperature to the combined mother liquors from (a) and (b) and the reaction mixture was stirred under reflux for another 19 hours. After the addition of approximately 6500 g chlorobenzene recovered from (a) and (b), the reaction mixture was stirred under reflux for another hour. Further working up was carried out as described in (a).

Yield: 1012 g (102%, based on urea used).

The yield of more than 100% is explained by the fact that the mother liquors from (a) and (b) contain dissolved product which was precipitated in the further reaction. NH value (HClO4/glacial acetic acid): 390 mg KOH/g. Residual 2,4-TDA content (HPLC): 0.158% by weight.

Example 6 (Comparison)

(Less preferred reaction conditions)

200 g (1.64 moles) tolylene-2,4-diamine (2,4-TDA) and 49 g (0.816 moles) urea (molar ratio 2,4-TDA/urea 2.01:1) were added at room temperature to 1334 g chlorobenzene (15 parts by weight 2,4-TDA, based on 100 parts by weight chlorobenzene). The reaction mixture was stirred under reflux for 5 hours. The precipitated product was filtered off hot and washed with petroleum ether.

Yield: 90 g (41%, based on urea used).

NH value (HClO4/glacial acetic acid): 274 mg KOH/g (theoretical 416 mg KOH/g).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an N,N'-bis-(3-aminophenyl)-urea compound corresponding to formula (I)

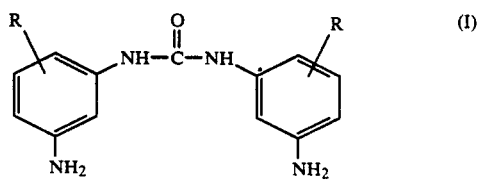

wherein

R represents a linear or branched C1-C6 alkyl group in the 2-, 4- and/or 6-position with urea in a molar ratio of greater than 2:1 in chlorobenzene as solvent to form a compound which precipitates out of chlorobenzene and recovering the precipitated compound.

2. The process of claim 1 wherein the molar ratio of said m-phenylene diamine to urea is greater than 3:1.

3. The process of claim 1 wherein said alkyl group is in the 4-and/or 6-position.

4. The process of claim 2 wherein said alkyl group is in the 4- and/or 6-position.

5. The process of claim 1 wherein R represents a methyl group.

6. The process of claim 2 wherein R represents a methyl group.

7. The process of claim 3 wherein R represents a methyl group.

8. The process of claim 4 wherein R represents a methyl group.

* * * * *

UNITED STATES PATENT AND TRADEMARK OFFICE
CERTIFICATE OF CORRECTION

PATENT NO. : 4,994,611
DATED : February 19, 1991
INVENTOR(S) : Andreas Ruckes et al It is certified that error appears in the above-indentified patent and that said Letters Patent is hereby corrected as shown below:

At column 2, line 1, delete "BaCl2" and insert --$BaCl_2$--.

At column 4, line 33, delete "fiber" and insert --filter--.

IN THE CLAIMS:

In Claim 1, at column 6, line 44, after "alkyl group" insert --which is--.

In Claim 1, at column 6, line 45, after "6-position", begin a new line and insert --which comprises reacting an m-phenylene diamine having a $C_1$-$C_6$ alkyl group in the 2-, 4- and/or 6-position--.

Signed and Sealed this

Twelfth Day of November, 1996

BRUCE LEHMAN

Attest:

Attesting Officer          Commissioner of Patents and Trademarks